US010016203B2

(12) United States Patent
Esposito (10) Patent No.: US 10,016,203 B2
(45) Date of Patent: Jul. 10, 2018

(54) TOURNIQUET AND METHOD OF USE

(71) Applicant: COMPOSITE RESOURCES, INC., Rock Hill, SC (US)

(72) Inventor: Mark Esposito, Fraser, CO (US)

(73) Assignee: Composite Resources, Inc., Rock Hill, SC (US)

( * ) Notice: Subject to any disclaimer, the term of this patent is extended or adjusted under 35 U.S.C. 154(b) by 0 days.

(21) Appl. No.: 14/526,295

(22) Filed: Oct. 28, 2014

(65) Prior Publication Data

US 2016/0302799 A1 Oct. 20, 2016

Related U.S. Application Data (60) Continuation of application No. 12/954,574, filed on Nov. 24, 2010, now Pat. No. 8,888,807, which is a division of application No. 11/147,806, filed on Jun. 6, 2005, now Pat. No. 7,842,067.

(60) Provisional application No. 60/521,630, filed on Jun. 8, 2004.

(51) Int. Cl.
A61B 17/132 (2006.01)

(52) U.S. Cl.
CPC ...... *A61B 17/1327* (2013.01); *A61B 17/1322* (2013.01)

(58) Field of Classification Search
CPC ........ A61F 5/30–5/34; A61B 17/132–17/1355
See application file for complete search history.

(56) References Cited

U.S. PATENT DOCUMENTS

| | | |
|---|---|---|
| 35,038 A | 4/1862 | Pierce |
| 35,048 A | 4/1862 | Pierce |
| 1,500,629 A | 11/1923 | Levy |
| 1,569,131 A | 1/1926 | Nord |
| 1,606,841 A | 11/1926 | Newton |
| 1,607,996 A | 11/1926 | Morgenthaler |

(Continued)

FOREIGN PATENT DOCUMENTS

| | | |
|---|---|---|
| BE | 400213 | 1/1934 |
| CA | 2542058 | 6/2005 |

(Continued)

OTHER PUBLICATIONS

ISR & Written Opinion dated Oct. 3, 2008, for PCT/US2005/020111.

*Primary Examiner* — Victor Nguyen
*Assistant Examiner* — Jonathan Hollm
(74) *Attorney, Agent, or Firm* — Nexsen Pruet, LLC; Michael A. Mann; William Y. Klett, III (57) ABSTRACT

A tourniquet for restricting a flow of blood in a body part is presented. In accordance with embodiments of the present invention, the tourniquet comprises a first elongated member, and a second elongated member in slidable engagement with the first elongated member. In addition, the tourniquet includes a tensioning mechanism connected to the second elongated member, wherein a compressive force is applied to the body part upon applying a tensile force to the second elongated member using the tensioning mechanism. The tourniquet is suited for emergency use, and may be applied by using only one hand. Thus, the tourniquet may be applied, manipulated and tightened by the wearer, even if the wearer is limited to the use of a single hand.

13 Claims, 7 Drawing Sheets

(56) References Cited

U.S. PATENT DOCUMENTS

| | | | |
|---|---|---|---|
| 1,698,813 A * | 1/1929 | Gouirand | B65D 63/08 24/269 |
| 2,113,534 A | 4/1938 | Brown | |
| 2,387,428 A * | 10/1945 | Brothers | A61B 17/1327 606/203 |
| 2,480,430 A * | 8/1949 | Walters | A61B 17/1325 606/203 |
| 3,756,239 A | 9/1973 | Smythe | |
| 3,930,506 A | 1/1976 | Overend | |
| 4,102,343 A | 7/1978 | Schneider | |
| 4,242,039 A | 12/1980 | Villard et al. | |
| 4,273,130 A * | 6/1981 | Simpson | A61B 17/1322 128/DIG. 15 |
| 4,479,495 A | 10/1984 | Isaacson | |
| 4,526,165 A | 7/1985 | Mielnik et al. | |
| 4,628,918 A | 12/1986 | Johnson, Jr. | |
| 4,640,281 A | 2/1987 | Sturm et al. | |
| 5,234,459 A | 8/1993 | Lee | |
| 5,295,996 A | 3/1994 | Blair | |
| D381,427 S | 7/1997 | Marrero | |
| 5,695,520 A | 12/1997 | Bruckner et al. | |
| 6,068,646 A | 5/2000 | Lam | |
| 6,189,538 B1 | 2/2001 | Thorpe | |
| 6,544,188 B1 | 4/2003 | Chesney et al. | |
| 6,602,214 B2 | 8/2003 | Heinz et al. | |
| 6,682,547 B2 | 1/2004 | McEwen et al. | |
| 6,746,470 B2 | 6/2004 | McEwen et al. | |
| 6,796,993 B2 | 9/2004 | Lambroza | |
| 6,833,001 B1 | 12/2004 | Chao | |
| 6,884,254 B2 | 4/2005 | Brooks | |
| 6,899,720 B1 * | 5/2005 | McMillan | A61B 17/1322 606/203 |
| 6,960,223 B1 | 11/2005 | Ambach | |
| 7,618,384 B2 | 11/2009 | Nardi et al. | |
| 7,763,046 B2 | 7/2010 | Schouten et al. | |
| 7,842,067 B2 * | 11/2010 | Esposito | A61B 17/1327 606/203 |
| 7,892,253 B2 * | 2/2011 | Esposito | A61B 17/1327 606/203 |
| 7,927,295 B2 | 4/2011 | Bates et al. | |
| 8,314,283 B2 | 11/2012 | Kingsford et al. | |
| 2001/0041910 A1 | 11/2001 | McEwen | |
| 2002/0188315 A1 | 12/2002 | Guzman et al. | |
| 2003/0028215 A1 | 2/2003 | Brooks | |
| 2003/0139766 A1 | 7/2003 | McEwen et al. | |
| 2003/0144691 A1 | 7/2003 | Lambroza | |
| 2003/0153936 A1 | 8/2003 | El-Galley | |
| 2005/0240217 A1 | 10/2005 | Jennifer et al. | |
| 2005/0267518 A1 | 12/2005 | Wright et al. | |
| 2008/0221612 A1 | 9/2008 | Rose | |
| 2010/0241032 A1 | 9/2010 | Lee et al. | |
| 2012/0089109 A1 | 4/2012 | Turner et al. | |

FOREIGN PATENT DOCUMENTS

| | | |
|---|---|---|
| DE | 3232418 | 9/1982 |
| GB | 2027149 A | 2/1980 |

* cited by examiner

TOURNIQUET AND METHOD OF USE

CROSS REFERENCE TO RELATED APPLICATION

The present application is a continuation application of U.S. application Ser. No. 12/954,574 filed on Nov. 24, 2010, which is a divisional application of U.S. patent application Ser. No. 11/147,806 filed on Jun. 6, 2005, now U.S. Pat. No. 7,842,067, which claims the benefit of U.S. Provisional Application No. 60/521,630 filed on Jun. 8, 2004, all of which are incorporated herein by reference in their entireties.

FIELD OF THE INVENTION

The present invention relates to a novel flow restriction device, and more particularly, to a novel tourniquet device for restricting the flow of blood.

BACKGROUND

Loss of blood is a major cause of death in emergency situations in which the injured person is alone or medical assistance is not immediately available. The use of a tourniquet to stop blood loss from an injured arm or leg is a well-known technique for preventing death in these situations. In general, for emergency use where the victim is alone, the victim must be able to apply the tourniquet to his or her own arm or leg and occlude blood flow using only one hand.

Tourniquets of the prior art generate inward radial compression on the limb by being put into high levels of circumferential tension when wrapped around the limb. As the pressure on the limb increases, the friction between the strap and the limb also increases, causing the underlying soft tissue to move with the strap as it is drawn tight. This tends to draw soft tissues underlying the strap into the ratchet or buckle device, pinching the soft tissue and creating a region of very high localized pressure which will cause unnecessary injury. This effect may also create high shearing stresses in the underlying soft tissues, increasing the probability of nerve and tissue injury. Friction between the strap and the limb may also create regions of low pressure by preventing tension from being distributed evenly in the strap around the entire limb circumference, and as a result, arterial blood may still flow through these low pressure regions although overall strap tension is very high. In general, the application of uneven or non-uniform application of pressure around the limb leads to the need for unnecessarily high overall tourniquet pressures to reliably and predictably stop arterial blood flow, and this need for unnecessarily high pressure increases the probability of a range of unnecessary injuries to nerves, muscles and the limb.

The use of a tourniquet in many emergency situations, including many recreational activities, such as hiking, rock climbing and camping, imposes a weight restriction on the tourniquet. Simply stated, if a tourniquet is too bulky or has an excessive weight, the potential user, such as a hiker, will not pack and carry the tourniquet with them. Therefore, there is a need of a relatively small and light-weight tourniquet that can be easily packed and carried, and subsequently used at remote locations, if necessary.

Accordingly, there is a need for an emergency, light-weight tourniquet that provides improved radial pressure to the wounded limb, thereby restricting blood flow to the limb. Furthermore, there is a need for such a tourniquet that can be applied by the victim using one hand.

SUMMARY OF THE INVENTION

These and other needs are addressed by the various embodiments and configurations of the present invention. The present invention comprises a tourniquet for restricting the flow of blood in a body part, such as a person's arm or leg. Thus, in accordance with embodiments of the present invention, a tourniquet for restricting a flow of blood in a body part is provided, the tourniquet comprising a first elongated member including a buckle, and a second elongated member slidably connected to the first elongated member. In addition, the tourniquet comprises a tensioning mechanism connected to the second elongated member, wherein a compressive force is applied to the body part upon applying a tensile force to the second elongated member using the tensioning mechanism, and wherein the compressive force restricts the flow of blood in the body part.

In accordance with embodiments of the present invention, the tensioning mechanism may comprise a windlass or a ratchet. In addition, for tourniquets utilizing a windlass as the tensioning mechanism, the tourniquet may also comprise a securing mechanism interconnected to the first elongated member, wherein the securing mechanism is adapted for securing the windlass after application of a tensile force to the second elongated member. In accordance with embodiments of the present invention, the securing mechanism comprises at least one hooked catch, or a securing strap, or at least one hooked catch and a securing strap. When used, the securing strap is preferably interconnected to the outer sleeve and is preferably oriented transversely to a longitudinal axis of the outer sleeve, wherein the securing strap is adapted to secure the windlass.

In accordance with embodiments of the present invention, the second elongated member forms a loop running from a first end of the first elongated member to the buckle and back to the first end of the first elongated member. Alternatively, in accordance with embodiments of the present invention, the second elongated member comprises at least a first portion extending from a first end of the first elongated member to the tensioning mechanism, wherein the first portion does not extend back to the first end of the first elongated member. In addition, in accordance with embodiments of the present invention, the second elongated member may comprise a second portion extending from the tensioning mechanism to the buckle. Finally, at least in some embodiments, the second portion of the second elongated member forms a loop between the buckle and the tensioning mechanism.

The present invention includes a variety of possible configurations. Thus, in accordance with embodiments of the present invention, a tourniquet for restricting a flow of blood in a body part is provided, the tourniquet comprising a means for circumferentially surrounding the body part, a means for compressing the body part, wherein the means for compressing slidably engages the means for circumferentially surrounding. In addition, the tourniquet comprises a means for tensioning the means for compressing, wherein applying a tensile force to the means for compressing using the means for tensioning applies a compressive force to the body part to restrict the flow of blood in the body part. In addition, the tourniquet preferably includes a means for securing the means for tensioning. In addition, the means for circumferentially surrounding preferably comprises a means for looping the means for circumferentially surrounding around the body part, as for example, a buckle or a ring. In addition, in accordance with embodiments of the present invention, the means for circumferentially surrounding comprises a means for fastening a portion of a first surface of the means for circumferentially surrounding to a second portion of the first surface of the means for circumferentially surrounding.

In accordance with embodiments of the present invention, the tourniquet uses in outer sleeve that is connected to an inner strap. Thus, in accordance with embodiments of the present invention, a tourniquet for restricting a flow of blood in a body part is provided, the tourniquet comprising an outer sleeve, an inner strap slidably connected to the outer sleeve, and a windlass connected to the inner strap, wherein a compressive force is applied to the body part upon applying a tensile force to the inner strap using the windlass, wherein the compressive force restricts the flow of blood in the body part.

In accordance with embodiments of the present invention, the outer sleeve comprises an upper panel connected to a lower panel, wherein at least a portion of the upper panel comprises hook and loop fasteners. In at least one embodiment, the hook and loop fasteners comprise OMNI-TAPE® (Velcro Industries B.V., Amsterdam, Netherlands).

In accordance with embodiments of the present invention, a tourniquet for restricting a flow of blood in a body part is provided, the tourniquet comprising a first elongated member comprising: (a) a surface comprising both hook and loop structures; (b) a first end for looping through a second end comprising a buckle; and (c) a pocket. In addition, the tourniquet comprises a second elongated member positioned in the pocket, wherein a portion of the second elongated member is connected to the first end of the first elongated member. In addition, the tourniquet comprises a windlass engaging the second elongated member, wherein the windlass is rotated to provide a tensile force in the second elongated member, wherein a compressive force is applied to the body part restricting the flow of blood in the body part. In addition, the tourniquet comprises at least one hooked catch or a securing strap interconnected to the first elongated member for engaging a portion of the windlass and preventing a return rotation of the windlass after applying the tensile force.

The present invention also includes a method of restricting a flow of blood in a body part. Thus, in accordance with embodiments of the present invention, a method of restricting a flow of blood to a body part is provided, the method comprising wrapping a first elongated member around the body part and looping a first portion of the first elongated member through a buckle. In addition, the method includes detachably attaching the first portion of the elongated member to a second portion of the elongated member. In addition, the method includes operating a tensioning mechanism connected to a second elongated member slidably positioned within the first elongated member, wherein the tensioning mechanism develops a tensile force in the second elongated member, and wherein a compressive force is applied to the body part restricting the flow of blood in the body part. The method also preferably includes securing the tensioning mechanism using a hooked catch or a securing strap.

In accordance with embodiments of the present invention, a method of restricting a flow of blood to a body part is provided, the method comprising placing a first elongated member for contacting the body part around the body part, and positioning at least a portion of the first elongated member through a restraining mechanism connected to the first elongated member. The method further comprises operating a tensioning mechanism operatively connected to a second elongated member, the second elongated member not contacting the body part, the second elongated member slidably engaging the first elongated member, wherein the tensioning mechanism develops a tensile force in at least a portion of the second elongated member, and wherein a compressive force is applied to the body part restricting the flow of blood in the body part.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

The drawings are not necessarily to scale, and may, in part, include exaggerated dimensions for clarity.

DETAILED DESCRIPTION OF THE INVENTION

The present invention comprises a tourniquet that can be manipulated and tightened by the user, including the victim, using one hand, if necessary. In addition, the tourniquet provides improved circulation stoppage by way of an inner tightening strap positioned within a sleeve.

Figures 1, 2, 3:
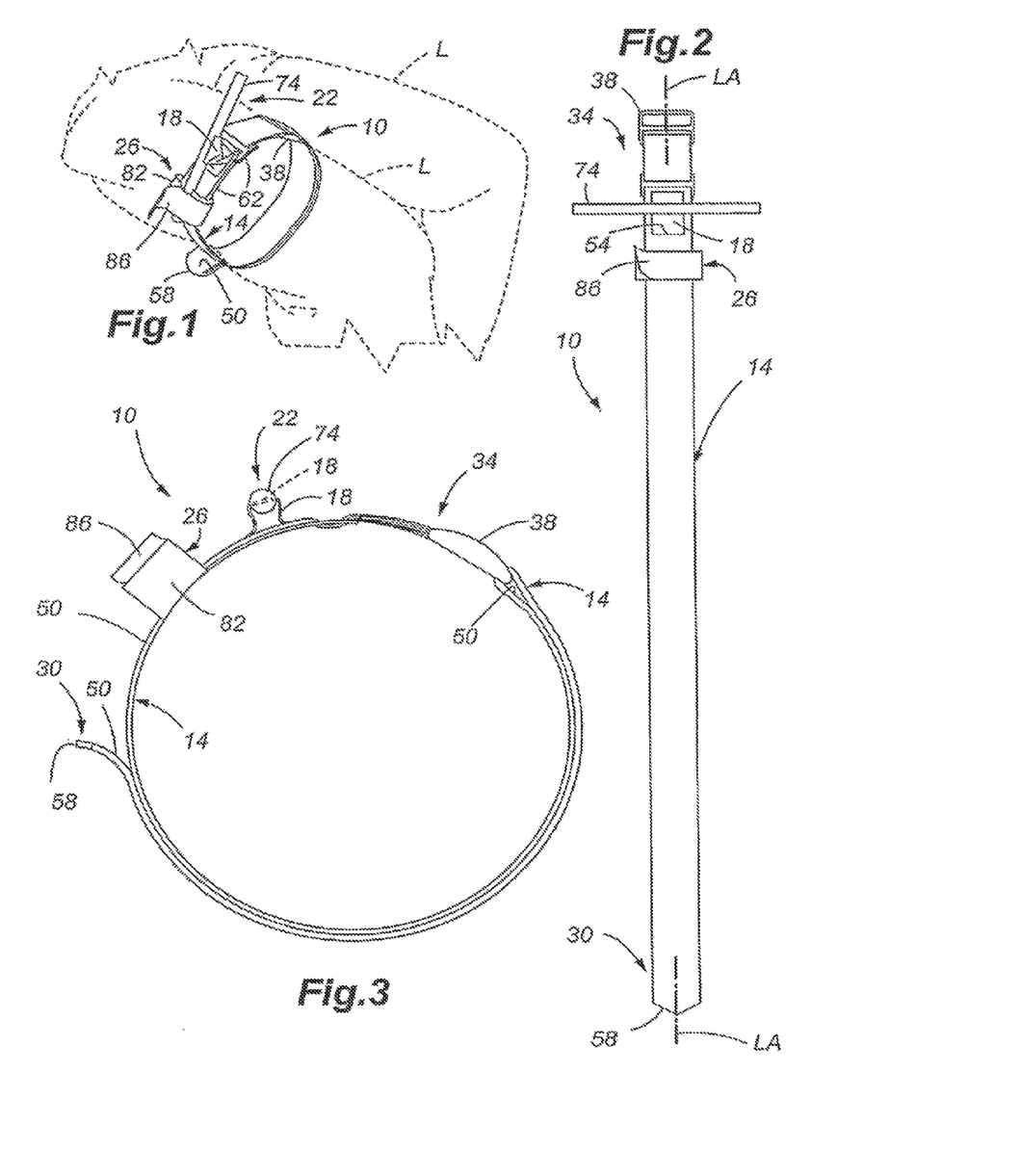
FIG. 1 is a perspective view of an embodiment of the present invention applied to a person's right leg (as shown in dashed lines)
FIG. 2 is a plan view of the device shown in FIG. 1, where the device is stretched out along its longitudinal axis.
FIG. 3 is a side elevation view of the device shown in FIG. 1, where the device is shown prior to tightening the device using the windlass.

Referring now to FIG. 1, a tourniquet 10 in accordance with embodiments of the present invention is shown. The tourniquet 10 comprises a first elongated member or an outer sleeve 14, a second elongated member, inner tightening member or inner strap 18, a tightening mechanism 22 and a securing mechanism 26. As shown in FIG. 1, the tourniquet 10 can be applied to an appendage, as for example, leg L, and then tightened to restrict the flow of blood to the leg L.

Referring now to FIG. 2, the tourniquet 10 is shown prior to use, or in a stretched-out orientation. The outer sleeve 14 comprises a longitudinally extensive material having a first end 30 and a second end 34. In accordance with embodiments of the present invention, the second end 34 includes a restraining mechanism, such as a ring or buckle 38. When the tourniquet 10 is applied to a limb, such as leg L shown in FIG. 1, the first end 30 is looped through the buckle 38 and pulled tight around the appendage, thus providing a means for circumferentially surrounding or encircling the limb. FIG. 3 depicts the tourniquet 10 after the first end 30 has been looped through the buckle 38.

Figure 4:
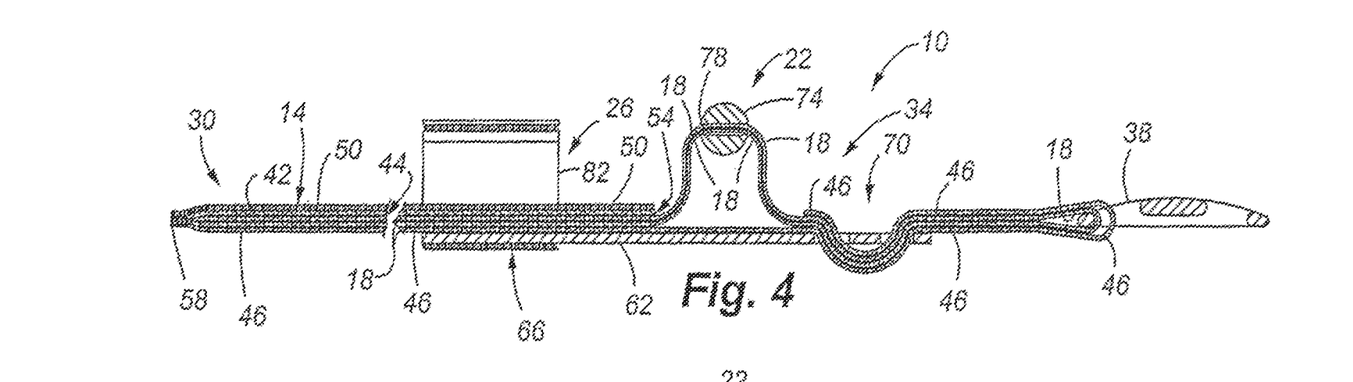
FIG. 4 is a cross sectional view of the device shown in FIG. 2 with the windlass in an unwound position.

Referring now to FIG. 4, in accordance with embodiments of the present invention, the outer sleeve 14 may be formed of two panels comprising an upper or first panel 42 and a lower or second panel 46. The edges of the panels 42 and 46 are connected, as for example, by sewing, glueing, stapling, clamping, or heat/ultra-sound (sonic) welding, or combinations thereof. Outer sleeve 14 includes a pocket, interior area or inner space 44 between the panels 42 and 46. The first panel 42 comprises an outer surface 50 that preferably includes hook and loop structures. More preferably, the outer surface 50 comprises both hook structures and loop structures along substantially the entire length of the outer sleeve 14 between the first end 30 and an opening 54 where the inner strap 18 is exposed between the first panel 42 and second panel 46 of the outer sleeve 14. Thus, when the first end 30 of the outer sleeve 14 is looped through the buckle 38, the outer surface 50 may be applied to itself, thereby securing the position of the outer sleeve 14. By way of example and not limitation, the first panel 42 may comprise a length of OMNI-TAPE® (Velcro Industries B.V., Amsterdam, Netherlands), wherein the fastening surface comprises both hook and loop structures on the outer surface 50 as depicted in FIG. 4. The use of a combination of both hook and loop structures on the outer surface 50 of the outer sleeve 14 provides the advantage of the tourniquet being quickly adjustable when in use to accommodate a variety of size appendages, as for example, from a person's thigh to a person's forearm.

In use, to size the tourniquet to the appendage, the user simply wraps the tourniquet around the subject appendage, loops the first end 30 of the outer sleeve 14 through the buckle 38, pulls the tourniquet reasonably tight, and then presses the outer surface 50 together detachably interlocking first and second portions of the outer surface 50 together to interlock the hook and loop structures of the outer surface 50 within the region where the outer surface 50 overlaps beyond the buckle 38. As those skilled in the art will appreciate, although not preferred, the outer surface 50 of the outer sleeve 14 may be fitted with standard hook fasteners to match-up with corresponding standard loop fasteners; however, although within the scope of the present invention, the ability of a single tourniquet so modified to accommodate various size appendages would be limited. Nonetheless, such an issue could be addressed by manufacturing tourniquets of different sizes and/or providing tourniquets having different portions of the outer surface fitted with various lengths of hook material to match-up with corresponding portions of loop material. Alternatively, other means of fastening the overlapping portion of the outer sleeve may be provided, such as buttons, snaps, transverse straps etc., and such variations and modifications are within the scope of the present invention.

It is further noted that although the outer sleeve 14 is preferably formed of an upper or first panel 42 and a lower or second panel 46, the outer sleeve 14 may be formed of a single piece of material, as by way of example and not limitation, a piece of material that is folded over and seamed, thereby forming a pocket or inner space 44.

Referring still to FIG. 4, the inner strap 18 is shown between the first panel 42 and the second panel 46 of the outer sleeve 14. In accordance with at least one embodiment of the present invention, the inner strap 18 comprises a length of nylon binding strap (also known as nylon binding tape) that extends from first end 30 of the outer sleeve 14 to the buckle 38 and returns to the first end 30 such that the inner strap 18 comprises a loop. Although a substantially non-elastic nylon binding strap type of material is preferred for use as the inner strap 18, other elongated types of materials may be used, such as a section of rope, belt, tubing, hose, band, or combinations thereof, where such structures thereby form a means for compressing a body part. The ends of the inner strap 18 are preferably anchored only at the tip 58 of the first end 30 of outer sleeve 14, as for example, by sewing, glueing, stapling, clamping, or heat/ultra-sound (sonic) welding, or combinations thereof. Thus, the inner strap 18 can slide within the interior space 44 of the outer sleeve 14. Accordingly, the inner strap 18 comprises a material that has frictional characteristics allowing it to slide within the interior space 44 of the outer sleeve 14 when a tensile force is applied to the inner strap 18. Although not required, depending upon the types of materials used to form the outer sleeve 14 and the inner strap 18, the interior space 44 of the outer sleeve 14 may optionally include a substance, such as a powder or other lubricant, to assist with the frictional characteristics between the surfaces of the inner strap 18 and the interior space 44 of the outer sleeve 14.

In accordance with embodiments of the present invention, the tourniquet may comprise an inner strap 18 that extends through and end or a slit (not shown) at the first end 30, such as a slit in the upper or first panel 42 of the outer sleeve 14. The inner strap 18 may then be anchored at or proximate to the distal end of the lower or second panel 46. Alternatively, the slit (not shown) may be in the second panel 46 and the inner strap 18 anchored at or proximate to the distal end of the first panel 42.

In accordance with embodiments of the present invention, the tourniquet may be configured such that a single layer (i.e., not a loop) of material is used to form the inner strap 18. Here, a first end of the inner strap 18 is anchored at or near the tip 58 of the first end 30 of the outer sleeve 14, and a second end of the inner strap 18 is anchored at or near the buckle 38, with the middle portion not anchored to the outer sleeve 14, and thereby able to slide within the outer sleeve 14. The tensioning mechanism 22 can be used to tighten the inner strap 18, such as by winding the windlass 74 to develop a tension force in the inner strap 18.

Referring still to FIG. 4, in accordance with embodiments of the present invention, the tourniquet 10 preferably includes a base member 62. As by way of example and not limitation, the base member 62 may be formed of a KYDEX® (Kleerdex Company, LLC, Mount Laurel, N.J.) thermoplastic or moldable (as for example, injection molded) plastic type of material. A first end 66 of base member 62 preferably includes a securing mechanism 26, as will be discussed below. The second panel 46 of the outer sleeve 14 extends over at least a portion of the base member 62, passes through a means for looping, such as buckle 38, and folds back to a second end 70 of the base member 62. The edges of the second panel 46 between the buckle 38 and the second end 70 of the base member 62 are preferably connected, as for example, by sewing, glueing, stapling, clamping, or heat/ultra-sound (sonic) welding, thereby securing the second end 34 of the outer sleeve 14 to the buckle 38.

Referring still to FIG. 4, in accordance with embodiments of the present invention, the inner strap 18 emerges from the outer sleeve 14 at opening 54 where it is connected to the tightening mechanism 22. For the embodiment shown in FIG. 4, the tightening mechanism 22 comprises a windlass 74 that is shown in an unwound position. The windlass 74 preferably is comprised of a plastic material; however other types of materials are within the scope of the invention. In accordance with embodiments of the present invention, the inner strap 18 passes through a slot or aperture 78 in the windlass 74, and as described above, the inner strap 18 extends to and around the buckle 38.

Figure 7:
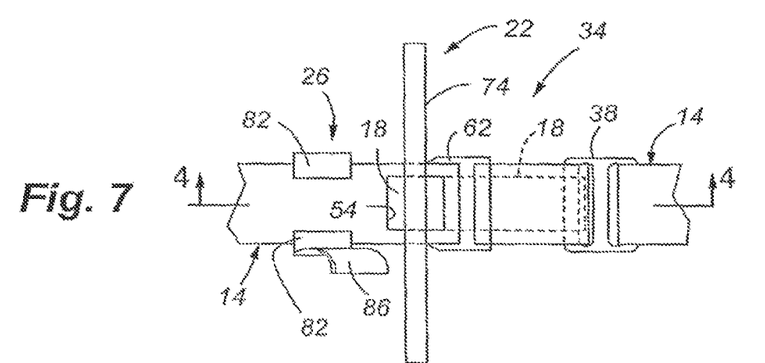
FIG. 7 is a plan view of the buckle end of the device with the outer sleeve looped through the buckle and the windlass in an unwound position.

Referring to FIG. 7, a plan view of the second end 34 of the outer sleeve 14 is shown. Here, the outer sleeve 14 has been looped through buckle 38; however, the tension mechanism 22, comprising a windlass 74, as will be described below, has not been wound to tighten the inner strap 18.

Figure 8:
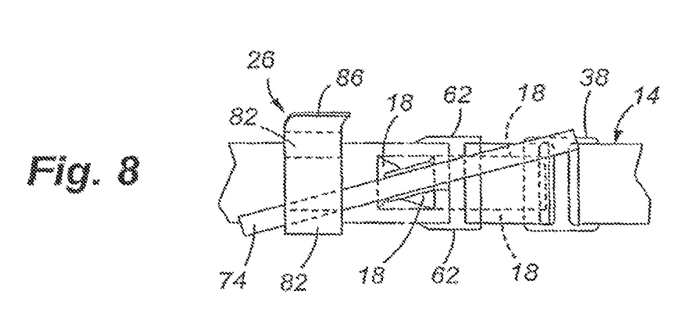
FIG. 8 is a plan view of the buckle end of the device with the outer sleeve looped through the buckle and the windlass in a wound position.

Referring now to FIG. 8, a plan view of the second end 34 of the outer sleeve is shown. Here, the outer sleeve 14 has been looped through buckle 38 and the windlass 74 has been partially wound, thereby applying a tensile force to the inner strap 18. Since the end of the inner strap 18 is secured to the tip 58 of the outer sleeve 14, when the windlass 74 is rotated, the inner strap 18 slides within the outer sleeve 14, essentially scrunching the outer sleeve 14 relative to the inner strap 18 as the inner strap 18 is increasingly tightened. The tightened inner strap 18 provides a substantially even radial compressive pressure to the limb to which the tourniquet 10 is being applied.

Figure 5:
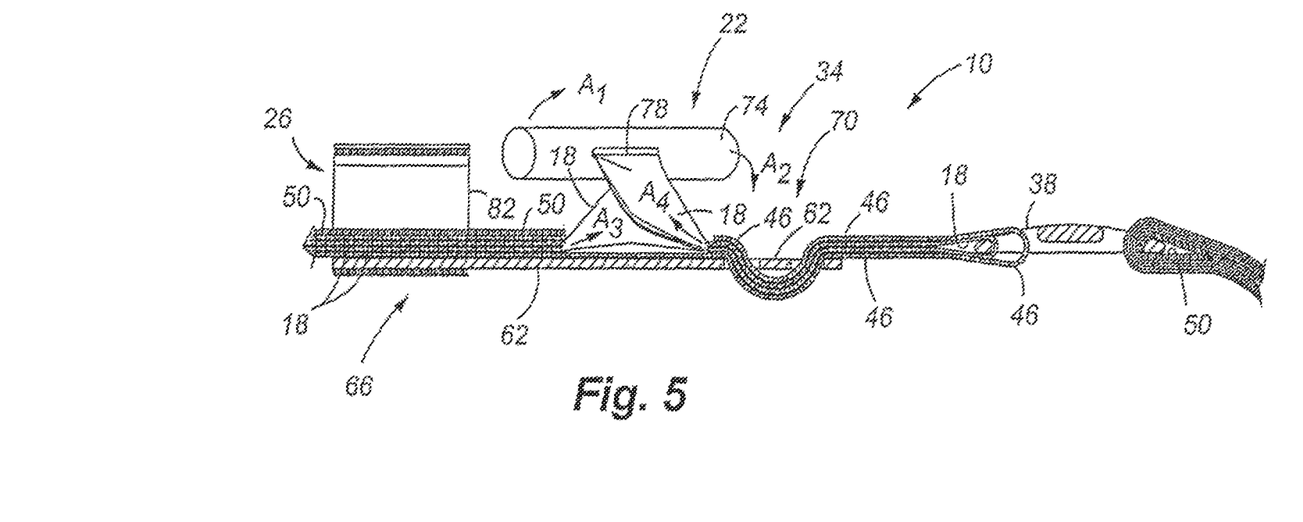
FIG. 5 is the same cross section view of the device as shown in FIG. 4, but with the outer sleeve looped through the buckle and the windlass partially rotated.

Referring now to FIG. 5, a cross sectional view of the tourniquet 10 is shown, including the second end 34 of tourniquet 10 with the windlass 74 in a partially wound position. More particularly, in use, after the first end 30 of the outer sleeve 14 is passed through the buckle 38 and secured around an appendage or limb, such as leg L shown in FIG. 1, the windlass 74 is rotated, such as in the direction of arrows A1 and A2, to apply a tensile force to at least a portion of the inner strap 18. Since the inner strap 18 is secured to the tip 58 of first end 30 of the outer sleeve 14, the inner strap 18 slides in the direction of arrows A3 and A4 within the outer sleeve 14 as the windlass 74 is rotated, thereby pulling the inner strap and providing a circumferentially applied compression force to the appendage. The tensile force is primarily developed in the portion of the inner strap 18 between the buckle 38 and the windlass 74, with typically a lesser amount of tension developed in the overlapping portion of the inner strap 18 between the buckle 38 and the tip 58, because when the inner strap 18 bends around the buckle 38 after being applied to an arm or leg, the bend tends to prevent the slippage of the inner strap 18 in the overlapped portion. After the windlass 74 is tightened, the tourniquet restricts the blood flow in the appendage. Accordingly, the tourniquet 10 of the present invention offers the advantage of an unlimited number of possible twists. More particularly, many tourniquets of the prior art are limited to a set number to twists by their windlass, thus limiting the amount of possible compression. As a result, such tourniquets of the prior art are venous tourniquets and are not suitable for arterial occlusion. However, the combination of the outer sleeve 14, inner strap 18 and tightening mechanism 22 of the present invention overcome this prior art limitation.

Figure 6:
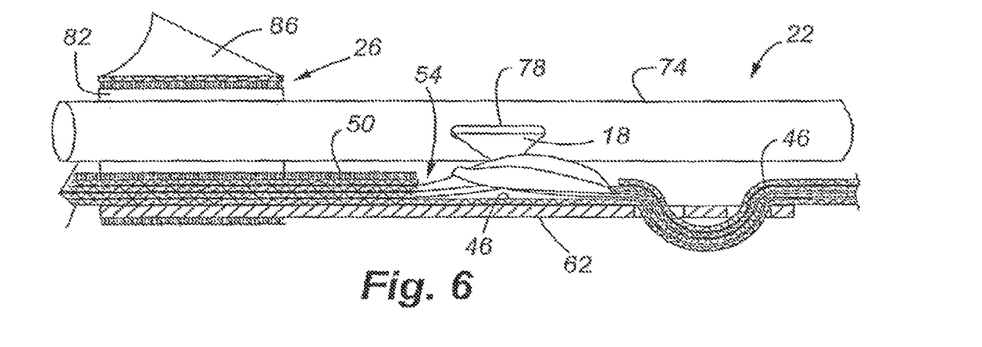
FIG. 6 is a cross sectional view of a portion of the device with the windlass in a wound position.

Referring now to FIG. 6, a cross sectional view of the second end 34 of tourniquet 10 is shown with the windlass 74 in a wound position. In accordance with embodiments of the present invention, after the windlass 74 has been sufficiently tightened to restrict the arterial blood flow in the appendage, the windlass 74 may be secured using securing mechanism 26. The securing mechanism 26 provides a means for securing or preventing the windlass 74 from unwinding. Thus, the securing mechanism 26 maintains the wound position of the windlass 74, and thereby maintains the tension in the inner strap 18.

In accordance with embodiments of the present invention, and as best seen in FIGS. 1, 7, and 8, the securing mechanism 26 preferably comprises a pair of opposing hooked catches 82 set substantially transverse to the longitudinal axis LA-LA of the tourniquet 10. More particularly, the hooked catches 82 are preferably sized to cup or hold the windlass, or a portion thereof, and prevent it from unwinding. Accordingly, the hooked catches 82 are sufficiently stiff to provide adequate resistance against the tensile force within the inner strap 18, as transferred to the hooked catches by the windlass 74. In accordance with embodiments of the present invention, and by way of example and not limitation, the hooked catches 82 may be formed of a KYDEX® thermoplastic material or molded plastic that may be integrally formed with, or otherwise connected to the base member 62. The preferred use of two opposing catches 82 allows the user to rotate the windlass 74 in either direction, with one of the two catches 82 always able to prevent the windlass 74 from unwinding. However, it is to be understood that the use of a single hooked catch 82 may be used and is within the scope of the present invention. For a single hooked catch 82, the user must rotate the windlass in the proper direction to allow the tension in the inner strap 18 to be resisted by the single hooked catch 82 once winding of the windlass and tensioning of the inner strap 18 is completed.

In accordance with embodiments of the present invention, the securing mechanism 26 may comprise a securing strap positioned transversely to a longitudinal axis LA-LA of the outer sleeve 14. As for example, a transversely oriented strap having hook and loop fastening portions, or an elastic band engaging a hook or button may be provided to secure the windlass 74 in its wound position.

In yet another possible alternative, a transversely oriented strap 86 may be used in combination with the hooked catches 82. Such a combination of structures allows the user to secure the windlass 74 and move about (or be moved by another person) with less concern of the windlass 74 dislodging from the hooked catches 82 and unwinding. In accordance with embodiments of the present invention, for hooked catches 82 used in combination with a transversely oriented strap 86, the outer surface of the hooked catches may comprise a hook or loop material, and a surface of the strap 86 may comprise a complementary hook or loop material to interlock with the material on the hooked catches 82.

Figure 9:
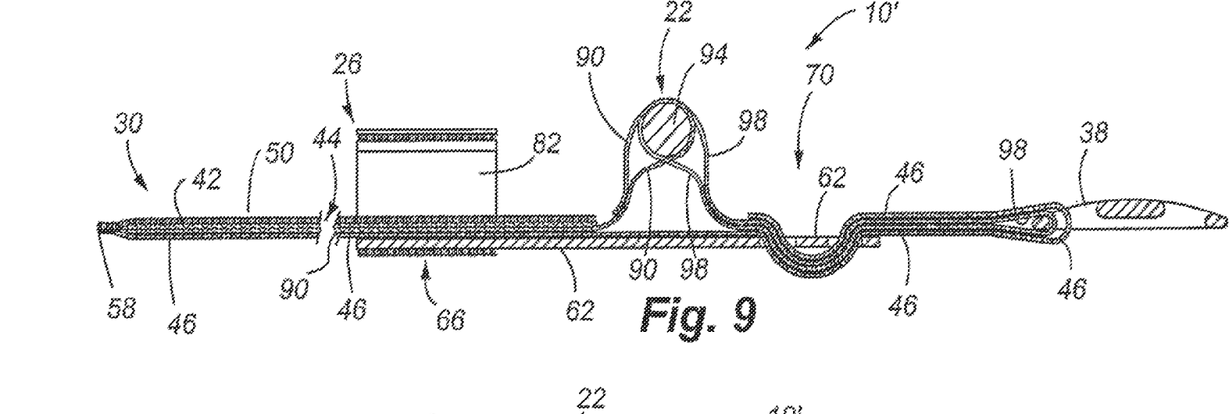
FIG. 9 is a cross sectional view of another tourniquet in accordance with embodiments of the present invention with the windlass in an unwound position.
Figure 10:
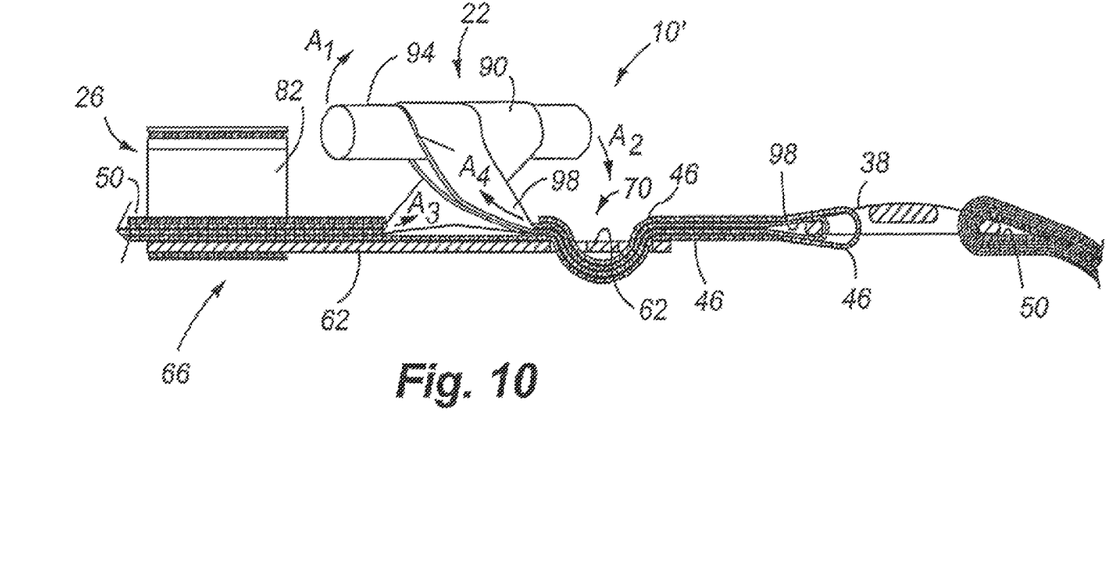
FIG. 10 is a cross sectional view of the tourniquet of FIG. 9 with the windlass in a partially wound position.

Referring now to FIGS. 9 and 10, a modified embodiment of the present invention is shown as tourniquet 10'. FIG. 9 shows the tourniquet 10' without having been tightened, and FIG. 10 shows the tourniquet 10' after it has been tightened. Tourniquet 10' comprises an outer sleeve 14 as described above, however, tourniquet 10' comprises an inner strap 90 that does not loop back and forth from the tip 58 of the outer sleeve 14 to the buckle 38 and back to the tip 58, but rather, only extends from the tip 58 to the securing mechanism 22. More particularly, the inner strap 90 is secured to, or proximate the tip 58, and extends from the tip 58 of the outer sleeve 14 to the tensioning mechanism 22, where the inner strap 90 ends at, or proximate to the tensioning mechanism 22. For the device illustrated in FIGS. 9 and 10, the inner strap 90 loops around or is otherwise connected to a windlass 94. As for example, the inner strap 90 loops around the windlass 94 of the tourniquet 10' where it is overlapped to and secured to itself, and/or connected to the windlass 94, as for example, by sewing, glueing, stapling, clamping, or heat/ultra-sound (sonic) welding, or combinations thereof.

In accordance with embodiments of the present invention, the tourniquet 10' preferably includes a second portion of an inner strap 98 that extends from buckle 38 to the windlass 94. The inner strap 98 may extend as an endless loop between the buckle 38 and the windlass 94. Alternatively, the inner strap 98 may not extend back and forth between the buckle 38 and windlass 94, but may only partially overlap and be secured to itself.

As with tourniquet 10, while a first end of the inner strap 90 is secured to the tip 58 of the outer sleeve 14, when the tightening mechanism 22 is used, as for example, when the windlass 94 is rotated, the inner strap 90, 98 slides within the outer sleeve 14, essentially scrunching the outer sleeve 14 relative to the inner strap 90, 98 as the inner strap 90, 98 is continued to be tightened. This provides substantially even radial compressive pressure to the limb to which the tourniquet 10' is being applied.

Figure 11:
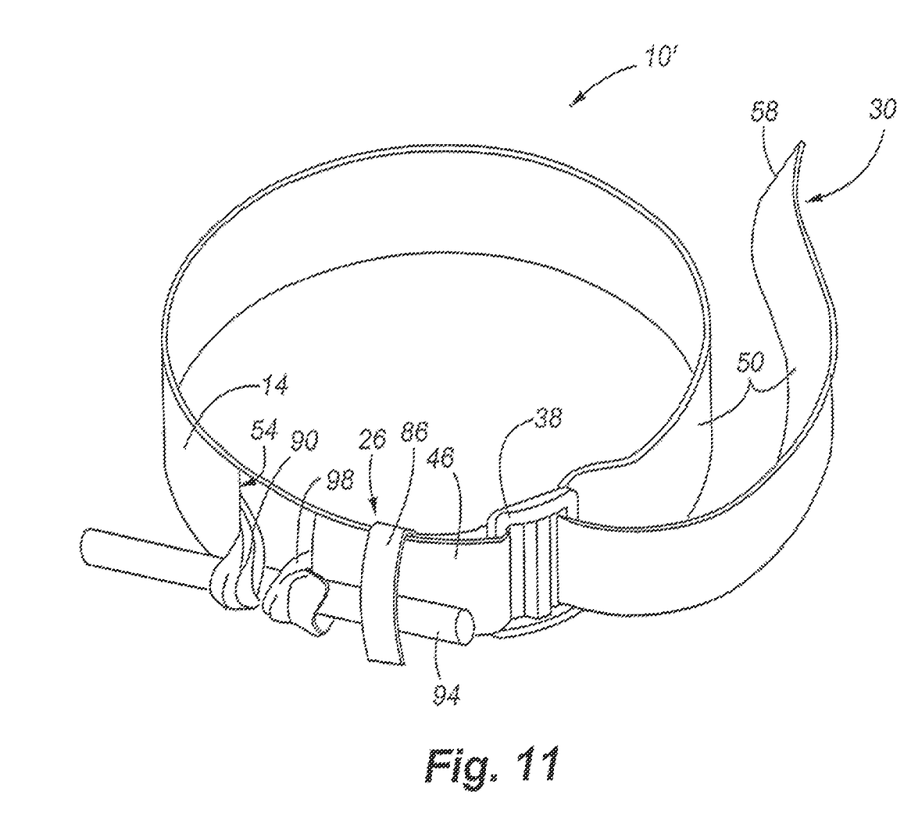
FIG. 11 is a perspective view of the tourniquet shown in FIG. 9 with the outer sleeve looped through the buckle and the windlass not rotated.
Figure 12:
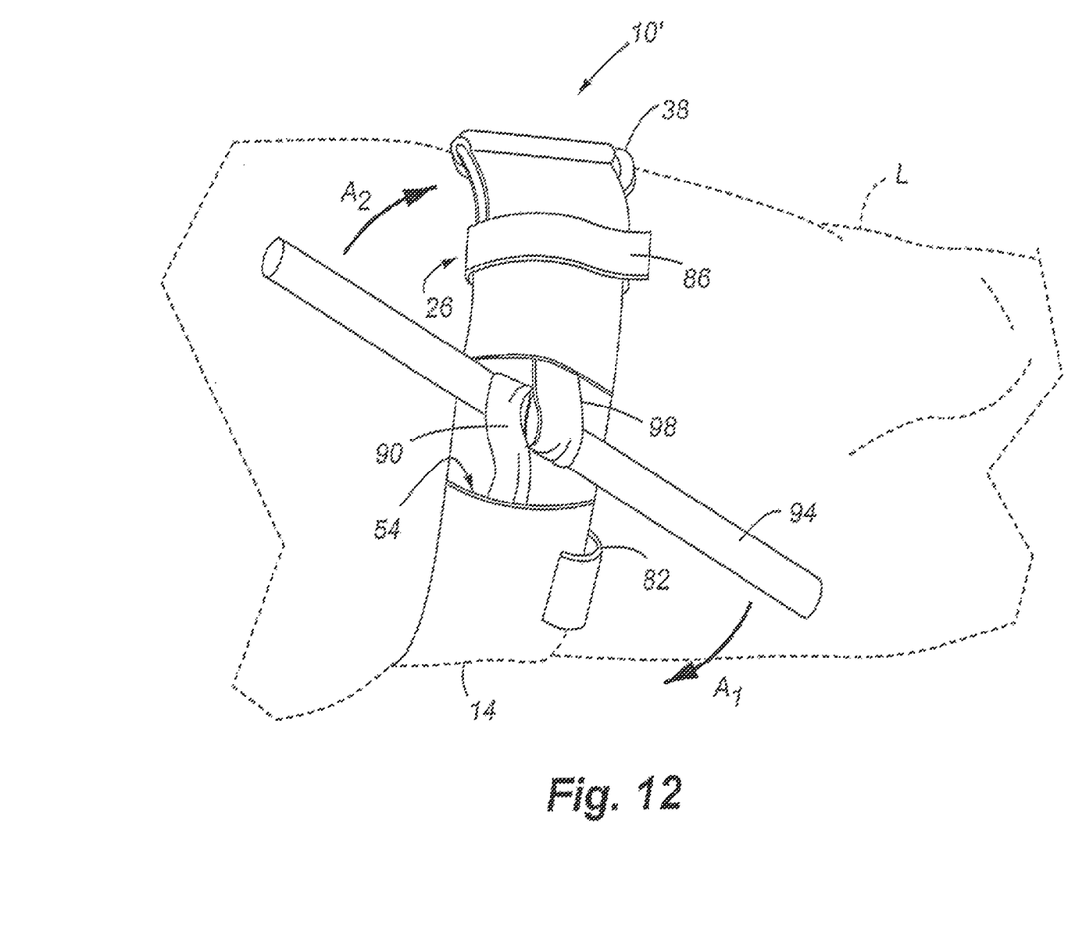
FIG. 12 is a perspective view of the tourniquet of FIG. 11 applied to a person's leg (as shown in dashed lines)

Referring now to FIG. 11, a perspective view of tourniquet 10' is shown after first end 30 is looped through buckle 38. As for example, in use the first end 30 is looped through buckle 38 and pressed together such that outer surface 50 is of outer sleeve 14 is secured to itself for the overlapping portion extending beyond the buckle 38. Referring now to FIG. 12, in use, the windlass 94 is tightened to apply a tensile force to inner strap 90, 98, and thereby apply a compressive force and restricting the blood flow to the limb, such as leg L.

Figure 13:
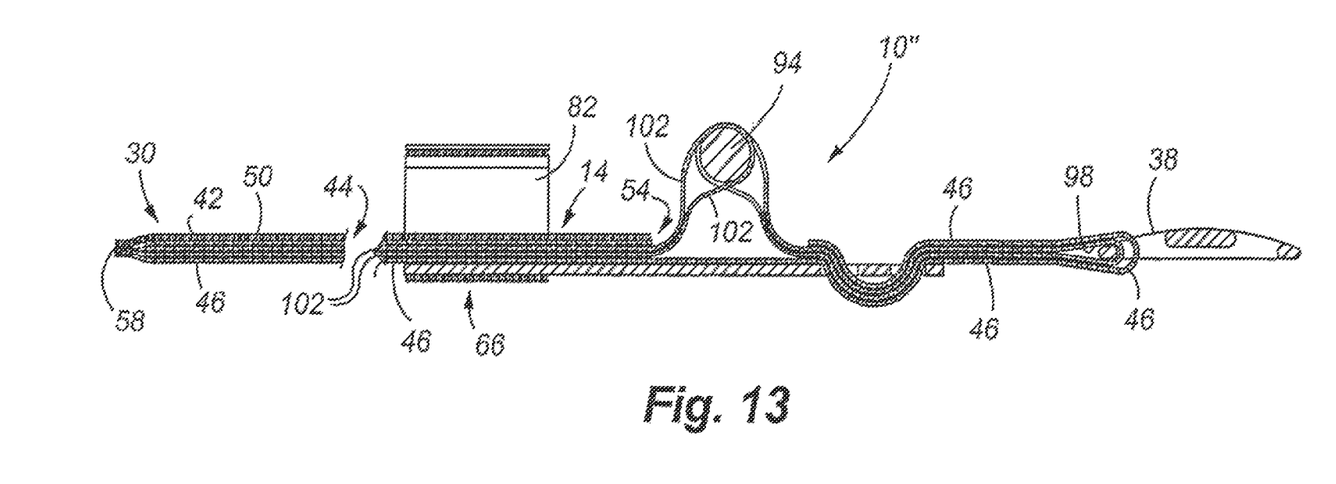
FIG. 13 is a cross sectional view of another tourniquet in accordance with embodiments of the present invention with the windlass in an unwound position.

Referring now to FIG. 13, yet another modified embodiment of the present invention is shown as tourniquet 10". Tourniquet 10" comprises a inner strap 102 that extends from tip 58 to securing mechanism 22 and back to tip 58, where the inner strap 102 is connected to the tip 58, such as by sewing, glueing, stapling, clamping, or heat/ultra-sound (sonic) welding, or combinations thereof. Thus, there are a variety of possible combinations and configurations for providing an inner strap, whether in one substantially continuous portion or in a plurality of portions, or as a loop or not as a loop, and such variations are all within the scope of the present invention.

In accordance with embodiments of the present invention, the tourniquet 10, 10', 10" preferably weighs less than about 160 grams, and more preferably, weighs less than about 100 grams, and more preferably yet, weighs less than about 60 grams. The relatively light-weight characteristics of the tourniquet 10, 10', 10" of the present invention lends itself to use by hikers and others that are packing and carrying limited supplies. Thus, the weight of the tourniquet 10, 10', and 10", in combination with its structure and functionality, is an important aspect of the present invention.

In use, to apply the tourniquet 10, 10', 10" to a body part and restrict the flow of blood in the body part, the user places or wraps the tourniquet 10, 10', 10" around the body part, loops the first end 30 of the outer sleeve 14 through the restraining mechanism or buckle 38, pulls the tourniquet reasonably tight, and then detachably attaches the overlapped outer surface 50 of outer sleeve 14 together by pressing the outer surface 50 together to interlock the hook and loop structures of the outer surface 50 within the region where the outer surface 50 overlaps beyond the buckle 38. The user then rotates the windlass 74, 94 and tightens the inner strap 18, 90, 98, 102 sufficiently to restrict the flow in the body part as may be necessary. The user may hold the windlass, in this position to maintain the compressive force on the limb; however, the user preferably secures the windlass in a tightened positioned by using a hooked catch and/or a securing strap. The tourniquets 10, 10', 10" of the present invention are preferably configured such that the outer sleeve 14 contacts the body part, and the inner strap 18, 90, 98, 102 does not contact the body part.

Figure 14:
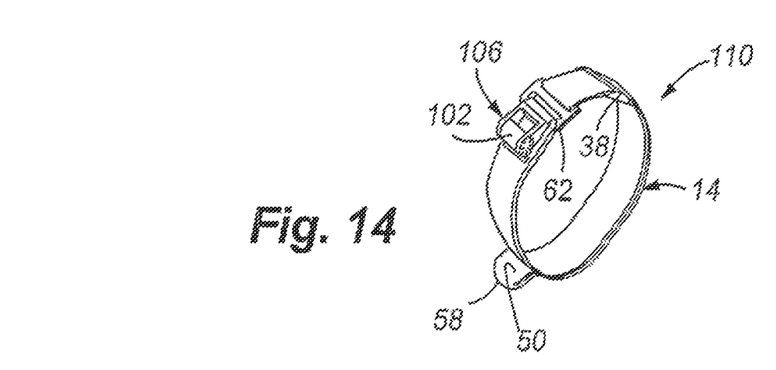
FIG. 14 is a perspective view of another tourniquet in accordance with embodiments of the present invention, wherein the tourniquet comprises a ratchet type of tensioning mechanism.

Referring now to FIG. 14, although preferred embodiments of the present invention utilize a windlass as the tightening mechanism 22, alternative means for tensioning or tightening may be provided. As for example, a ratchet mechanism 106 may be used, such as that shown in FIG. 14. Although potentially bulkier than a windlass 74, a ratchet mechanism 106 can be connected to an inner strap 102 and used to apply a tensile force to the inner strap 102, thus tightening the tourniquet 110. A ratchet tightening mechanism is described in U.S. Pat. No. 4,243,039, the contents of which is incorporated herein by reference in its entirety. See also Calkins et al., May 2000, "Evaluation of Possible Battlefield Tourniquet Systems for the Far-Forward Setting," *Military Medicine*, Vol. 165, 5:379, the contents of which is incorporated herein by reference in its entirety.

In accordance with embodiments of the present invention, a tension mechanism may be omitted. As for example, the inner strap may comprise an elastic cord (e.g., rubber hose) that is pulled by hand and locked in its tightened state. Accordingly, the tourniquet may comprise a securable clip (not shown), such as a biased cord restraint. The securable clip allows the user to pull the inner strap 18 and then engage the clip to hold the inner strap in its tensioned state.

The present invention has application for use in emergency medical situations for people. In addition, the invention also has application for use in veterinary medicine to apply a tourniquet to a body part or limb of an animal.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

What is claimed is:

1. A tourniquet for restricting a flow of blood in a body part, the tourniquet comprising:
   (a) an outer sleeve having a first end and second end and including an upper panel and a lower panel, said upper panel and said lower panel being spaced apart so as to define an inner space therebetween, said upper panel being connected to said lower panel, said outer sleeve carrying hook and loop structures;
   (b) an inner strap in slidable engagement with the outer sleeve, said inner strap being in said inner space between said upper panel and said lower panel of said outer sleeve, said inner strap having a first end anchored at said first end of said outer sleeve and an opposing second end of said inner strap anchored at said second end of said outer sleeve, wherein said inner strap is slidable between said upper panel and said lower panel, and wherein said outer sleeve has an opening between said upper panel and said lower panel where said inner strap is exposed;
   (c) a windlass connected to the inner strap at said opening in said outer sleeve, said windlass operable to pull said second end of said inner strap toward said windlass at said opening; and
   (d) a buckle carried by said first end of said outer sleeve, said buckle threaded to said second end of said outer sleeve, said outer sleeve and said buckle being securable to a body part, wherein said buckle and said outer sleeve are operable to apply a compressive force to a body part, and the windlass is operable to apply a tensile force to the inner strap, wherein the compressive force and the tensile force restrict the flow of blood in the body part.

2. The tourniquet as claimed in claim 1, further comprising at least one hooked catch interconnected to the outer sleeve, wherein said at least one hooked catch is operable to secure the windlass.

3. The tourniquet as claimed in claim 1, further comprising a securing strap interconnected to the outer sleeve and oriented transversely to a longitudinal axis of the outer sleeve, wherein the securing strap is operable to secure the windlass.

4. The tourniquet as claimed in claim 1, wherein the hook and loop structures comprises a single component hook and loop fastener having hook and loop on a common surface.

5. The tourniquet as claimed in claim 1, wherein the inner strap forms a loop extending from a first end of the outer sleeve to at least the windlass and back to the first end of the outer sleeve.

6. The tourniquet as claimed in claim 1, wherein the inner strap extends from a first end of the outer sleeve to at least the windlass, but does not form a loop back to the first end of the outer sleeve.

7. The tourniquet of claim 1, wherein said outer sleeve has a longitudinal axis and wherein said upper panel and said lower panel are attached together and parallel to said longitudinal axis so said inner strap is slidable in said inner space between said upper panel and said lower panel.

8. The tourniquet of claim 1, wherein said inner strap is made of nylon binding tape.

9. The tourniquet of claim 1, wherein said first end of said inner strap is anchored at said first end of said outer sleeve and said second end of said inner strap is anchored at said buckle.

10. The tourniquet of claim 1, further comprising a lubricant in said inner space.

11. The tourniquet of claim 1, wherein said inner strap extends from said buckle to said first end of said outer sleeve and back to said buckle in a loop.

12. The tourniquet as claimed in claim 1, further comprising a pair of opposing hooked catches interconnected to the outer sleeve, wherein one hooked catch of said pair of opposing hooked catches is operable to secure said windlass.

13. A tourniquet for restricting a flow of blood in a body part, the tourniquet comprising:
   (a) an outer sleeve including a first end and an opposing second end, an upper panel and a lower panel, said upper panel being connected to said lower panel so as to define an inner space therebetween, said lower panel having a first portion and a second portion;
   (b) an inner strap in said inner space, said inner strap having a first end anchored at said first portion of said lower panel at said first end of said outer sleeve and an opposing second end of said inner strap anchored at said second portion of said lower panel at said second end of said outer sleeve, and said inner strap being operable to slide between said upper panel and said lower panel, said outer sleeve having an opening where said inner strap is exposed;
   (c) a windlass connected to the inner strap at said opening of said outer sleeve, wherein said windlass is operable to pull said second end of said inner strap toward said windlass through said opening; and
   (d) a buckle operable to be connected to said first end of said outer sleeve and to be threaded to said second end of said outer sleeve to secure said outer sleeve around a body part and, when so connected and threaded, to apply a compressive force to restrict flow of blood in the body part, and said windlass being operable to apply a tensile force to the inner strap to further restrict the flow of blood in the body part.

* * * * *